United States Patent [19]

Hayashi et al.

[11] 4,261,917

[45] Apr. 14, 1981

[54] PROCESS FOR MANUFACTURING A HIGHLY CONCENTRATED SULFATE SOLUTION OR SLURRY

[75] Inventors: Akira Hayashi, Sakura; Yoshio Acki, Tokyo; Kyozo Kitano, Chiba; Toshiaki Ogoshi, Funabashi, all of Japan

[73] Assignee: The Lion Fat & Oil Co., Ltd., Tokyo, Japan

[21] Appl. No.: 91,232

[22] Filed: Nov. 5, 1979

[30] Foreign Application Priority Data

Nov. 10, 1978 [JP] Japan .................................. 53/137843

[51] Int. Cl.³ .................... C07C 141/02; C07C 141/08
[52] U.S. Cl. ............................ 260/458 R; 260/459 R; 252/550
[58] Field of Search ........................ 260/458 R, 459 R

[56] References Cited

U.S. PATENT DOCUMENTS

| | | | |
|---|---|---|---|
| 3,919,125 | 11/1975 | Ashina et al. | 260/459 R |
| 4,153,625 | 5/1979 | Barton et al. | 260/459 R |
| 4,191,704 | 3/1980 | Mather et al. | 260/459 R |

*Primary Examiner*—Nicky Chan
*Attorney, Agent, or Firm*—Blanchard, Flynn, Thiel, Boutell & Tanis

[57] ABSTRACT

A process for manufacturing a highly concentrated sulfate solution or slurry which comprises neutralizing a sulfuric ester of higher alcohol or its ethoxylate with an aqueous caustic alkali solution, thereby preparing a crude neutralization product containing the sulfate in the range of from 45 wt. % to 55 wt. % and the caustic alkali in the range of from 1.5 wt. % to 3.5 wt. % and having a viscosity less than 50 poise; and commingling the resulting crude neutralization product with the sulfuric ester in the range of from 30 parts by weight to 100 parts by weight per 100 parts by weight of the crude neutralization product and a highly concentrated caustic alkali solution capable of sufficiently neutralizing the sulfuric ester, thereby reducing the quantity of sulfate contained in the resulting mixture in the range of from 60 wt. % to 75 wt. % and the quantity of caustic alkali contained therein less than 0.5 wt. % of the quantity of sulfate.

7 Claims, No Drawings

PROCESS FOR MANUFACTURING A HIGHLY CONCENTRATED SULFATE SOLUTION OR SLURRY

BACKGROUND OF THE INVENTION

The present invention relates to an improved process for manufacturing higher alcohol sulfate or higher alcohol ethoxysulfate. More particularly the present invention relates to a process for manufacturing an aqueous solution or slurry containing a caustic alkali salt of sulfuric ester of higher alcohol or its ethoxylate in a high concentration ranging from 60 wt.% to 75 wt.%.

The aqueous higher alcohol sulfate or higher alcohol ethoxysulfate solutions or slurries are generally manufactured by sulfating higher alcohols or higher alcohol ethoxylates with sulfur trioxide or chlorosulfonic acid and then neutralizing the resulting sulfates with an aqueous caustic alkali solution. The concentrations of aqueous solutions or slurries thereby obtained are practically limited to about 30 wt.% at the highest. This is because, when it is attempted to obtain higher concentrations, the reactants or products become so highly viscous that difficulties are brought about in handling them at the time of manufacturing, transporting products and so forth. Even if this problem be solved, however, it is preferable, from the viewpoints of not only production efficiencies but also storage or transportation economies, that the aqueous sulfate solutions or slurries should be manufactured with high concentrations.

Under these circumstances, a conventional method is proposed in order to achieve the manufacture of low-viscosity and yet high-concentration sulfate solution or slurry, said method comprising allowing a viscosity-lowering substance to co-exist at the time of neutralizing the sulfuric ester. In this connection, Japanese Patent Open No. 116383/1975 discloses the method comprising the use of polyethylene glycol, Japanese Patent Open No. 80285/1977 discloses the method comprising the use of excess caustic alkali, and Japanese Patent Open No. 5089/1978 discloses the method comprising the use of sulfuric acid or sodium sulfate respectively.

However, the aqueous solutions or slurries obtained by the above mentioned conventional methods are defective in that their concentrations are about 55 wt.% at the highest, and so, when they are more highly concentrated, their viscosities are extremely increased and thus their fluidities are lost and ultimately they are gelated. In addition, the aqueous solutions or slurries obtained by the aforesaid conventional methods are disadvantageous in that since those solutions or slurries necessarily contain viscosity-lowering substances as impurities, their usages are restricted.

SUMMARY OF THE INVENTION

The present invention provides a process for manufacturing an aqueous sulfate solution or slurry which is of higher concentration than those obtained by the above mentioned conventional methods and further possesses a fluidity sufficient to meet practical purposes.

In other words, the improved process for manufacturing an aqueous sulfate solution or slurry according to the present invention, which comprises neutralizing a sulfuric ester selected from sulfuric esters of higher alcohols and sulfuric esters of higher alcohol ethoxylates with caustic alkali, is characterized by the steps of:

(a) neutralizing said sulfuric ester with an aqueous caustic alkali solution, thereby preparing a crude neutralization product containing the sulfate in the range of from 45 wt.% to 55 wt.% and the caustic alkali in the range of from 1.5 wt.% to 3.5 wt.% and having a viscosity less than 50 poise; and (b) commingling the resulting crude neutralization product with the sulfuric ester in the range of from 30 parts by weight to 100 parts by weight per 100 parts by weight of the crude neutralization product and a highly concentrated caustic alkali solution capable of sufficiently neutralizing the sulfuric ester, thereby increasing the quantity of sulfate contained in the resulting mixture to the range of from 60 wt.% to 75 wt.% and the quantity of caustic alkali contained therein less than 0.5 wt.% of the quantity of sulfate.

DETAILED DESCRIPTION OF THE INVENTION

The crude neutralization product according to the present invention is conventionally prepared by neutralizing a sulfuric ester of higher alcohol and/or its ethoxylate with an aqueous caustic alkali solution, said sulfuric ester having been prepared by sulfating $C_{8-22}$ straight chain or branched chain natural or synthetic alcohol with sulfur trioxide or chlorosulfonic acid, or by sulfating higher alcohol ethoxylate with sulfur trioxide or chlorosulfonic acid, said higher alcohol ethoxylate comprising the addition of an average of 1 to 5 moles of $C_{2-4}$ alkylene oxide to said natural or synthetic alcohol. The crude neutralization product according to the present invention is exclusively required to have a sulfate concentration in the range of from about 45 wt.% to about 55 wt.%. A too high sulfate concentration is not desirable for practical use because the fluidity of the crude neutralization product per se is low, while a too low sulfate concentration is also not desirable because the quantity of sulfuric ester to be added to the crude neutralization product naturally will have to be increased, whereby the quantity of heat generated when neutralizing the sulfuric ester increases and the quality of the final product is thus deteriorated. The quantity of caustic alkali contained in the crude neutralization product is required to be in the range of from 1.5 wt.% to 3.5 wt.%, but the optimum concentration depends on the kind and quantity of the sulfate. The viscosity of the crude neutralization product is required to be less than 50 poise (at 50° C.). When the crude neutralization product has a viscosity higher than that, it becomes extremely difficult to obtain a homogeneous mixture of the sulfuric ester and the caustic alkali added thereto. And, in the preparation of the crude neutralization product according to the present invention it is recommended that an aqueous caustic alkali solution whose concentration is in the range of from 10 wt.% to 25 wt.% should be used for obtaining the crude neutralization product capable of satisfying the above described essential factors.

According to the present invention, the above mentioned crude neutralization product is mixed and added with sulfuric ester and a highly concentrated caustic alkali solution. The sulfuric ester used herein is prepared through the same process as employed in the preparation of the crude neutralization product which comprises sulfating higher alcohol or higher alcohol ethoxylate with sulfur trioxide or chlorosulfonic acid. The quantity of sulfuric ester added is selected from the range of from 30 parts by weight to 100 parts by weight per 100 parts by weight of the crude neutralization product so that the finally obtained aqueous solution or slurry may have a sulfate concentration in the range of from 60 wt.% to 75 wt.%. And, the quantity of the highly concentrated caustic alkali solution added is required to be capable of sufficiently converting the sulfuric ester added to the crude neutralization product into sulfate, and generally is so selected that the quantity of caustic alkali contained in the final product may be less than 0.5% by weight of the sulfate. In this connection, it is to be noted that when the quantity of caustic alkali is insufficient and so the final product is acidic, it is subject to quality deterioration during storage. On the other hand when the quantity of excess alkali contained in the final product is increased, the viscosity thereof rapidly rises in proportion thereto. In view of this, it is ideal that the final product should contain neither non-neutralized sulfuric ester nor excess alkali, but it is tolerable that the excess alkali is present in a quantity less than 0.5 wt.% of the sulfate contained in the final product, preferably less than 0.2 wt.% thereof, more preferably 0.1 wt.% thereof. And, in order that the sulfuric ester added to the crude neutralization product may be wholly converted into sulfate and further the excess alkali contained in the final product may be lessened below the predetermined quantity, it is practical that a solution having a concentration in the range of from about 30 wt.% to about 50 wt.% should be employed as the highly concentrated caustic alkali solution.

When the sulfuric ester and the highly concentrated caustic alkali solution are added to the crude neutralization product and mixed therewith, it is desirable that the crude neutralization product has been held in the range of from 30° C. to 60° C., the sulfuric ester has been held in the range of from 20° C. to 50° C., and the highly concentrated caustic alkali solution has been held in the range of from 0° to 50° C. respectively. As heat of neutralization is generated by the above mentioned adding and mixing, cooling is required so that the neutralization reaction may be carried out substantially within the range of from 30° C. to 70° C. The crude neutralization product is fully mixed with the sulfuric ester and the highly concentrated caustic alkali solution added to said product so that the sulfuric ester may wholly be converted into sulfate. Thereby it is made possible to obtain a final product having a viscosity less than about 200 poise, more particularly an aqueous solution or slurry containing sulfate in such a high concentration ranging from 60 wt.% to 75 wt.%.

As the industrial method for neutralizing the acid of anionic surface active agents there is generally employed the continuous neutralization method which comprises introducing material ingredients continuously into a mixer, passing the mixture discharged from the mixer through a heat exchanger for recovering a part thereof as product, and circulating the rest into the mixer. However, when the neutralization reaction product is highly viscous, removing the heat of neutralization and effecting uniform mixing of the ingredients become difficult. Due to this, there is caused the necessity for using a highly efficient heat exchanger and mixer. In particular, when neutralizing the sulfuric ester of an alcohol or the sulfuric ester of an alcohol ethoxylate which is liable to undergo hydrolysis, it is exclusively required that the neutralization reaction should be completed in an extremely short time. As a matter of course, therefore, the requirements exerted on the heat exchanger and the mixer are increased to the utmost.

According to the present invention, in contrast, in spite of the sulfate concentration of the finally obtained neutralization reaction product being in a high range of from 60 wt.% to 75 wt.%, as nearly half of the sulfate comes from the crude neutralization product and further the neutralization of the sulfuric ester is carried out in the presence of the relatively low-viscosity crude neutralization product, the heavy duty exerted on the mixer can be reduced and additionally the side reactions, such as hydrolysis or the like, can be substantially eliminated. What is more, the quantity of heat generated when neutralizing the sulfuric ester in accordance with the present invention, where the crude neutralization product is employed, is only about half of the quantity of heat generated when the sulfate contained in the final reaction product is wholly produced directly from sulfuric ester and caustic alkali without using the crude neutralization product, whereby the heavy duty exerted on the heat exchanger can also be lightened. Therefore, according to the present invention there can be obtained a highly concentrated sulfate solution or slurry suitable for storage or transportation, avoiding the troubles of especially increasing the capacities of the mixer and the heat exchanger and with no fear of color tone deterioration, hydrolysis and so forth.

EXAMPLE

A higher alcohol sulfuric ester was obtained by the sulfation of a higher alcohol having $C_{12}$ as its principal ingredient (trade name: Conol 20P, average molecular weight: 187, manufactured by New Japan Chemical Co., Ltd.) with gaseous $SO_3$. The thus obtained higher alcohol sulfuric ester and a caustic soda solution having a concentration of 20 wt.% were supplied to a mixer in the rates of 200 Kg/hr and 210 Kg/hr respectively. A part of the effluent from the mixer was cooled to about 50° C. by means of a heat exchanger and then circulated to the mixer. The rest was obtained as crude neutralization product.

Next, the above mentioned procedure was repeated varying the concentration and quantity of the caustic soda solution used, thereby preparing a variety of crude neutralization products which are different in respect of the sulfate (AI) content, caustic soda content and viscosity. The properties of the respective crude neutralization products are as shown in Table-1.

TABLE-1

| Crude neutralization product | A | B | C | D | E | F | G |
|---|---|---|---|---|---|---|---|
| AI content (wt. %) | 51 | 51 | 51 | 48 | 48 | 55 | 55 |
| Caustic soda content (wt. %) | 2.5 | 1.2 | 3.8 | 3.4 | 1.2 | 1.9 | 1.0 |
| Viscosity (40° C., poise) | 2.5 | 350 | 250 | 15 | 400 | 40 | 450 |

In addition, a variety of crude neutralization products were prepared through the same procedure by varying the kind of the sulfate used.

The properties of the respective crude neutralization products thus obtained are as shown in Table-2.

TABLE-2

| Crude neutralization product | AI content (wt. %) | Caustic soda content (wt. %) | Viscosity (40° C., poise) |
|---|---|---|---|
| H Sodium sulfate salt of synthetic alcohol (Dobanol 23* average molecular weight 194) | 51 | 3.0 | 25 |
| I Sodium sulfate salt of synthetic alcohol (Dobanol 45* average molecular weight 219) | 54 | 2.7 | 45 |
| J Sodium sulfate salt of ethylene oxide 1.5 mol additive (average molecular weight 285) of synthetic alcohol (Dobanol 45) | 51 | 2.6 | 30 |
| K Sodium sulfate salt of ethylene oxide 5 mol additive (average molecular weight 414) of synthetic alcohol (Dobanol 23) | 55 | 2.2 | 35 |

*manufactured by Mitsubishi Petrochemical Co., Ltd. of Japan.

Next, the crude neutralization products shown in Table-1 and Table-2, and the sulfuric ester and caustic soda solution (concentration 48 wt.%) used at the time of preparing said crude neutralization products were supplied to a mixer in their respective fixed rates. The effluent from the mixer was cooled to about 60° C. by means of a heat exchanger and then circulated to the mixer, during which a part was taken out thereof as product.

The kinds and quantities used of crude neutralization products put to experiments, quantities used of the sulfuric ester and the caustic soda solution and the properties of obtained products are as shown in Table-3.

In this connection, it is to be noted that the term "color tone" in both tables indicates the absorbancy; $(\log I/I_0) \times 10^3$ at 10% concentration.

TABLE-3

| Experiment No. | | 1 | 2 | 3 | 4 | 5 | 6 | 7 | 8 | 9 | 10 | 11 |
|---|---|---|---|---|---|---|---|---|---|---|---|---|
| Crude neutralization product | Kind | A | B | C | D | E | F | G | H | I | J | K |
| | Quantity (Kg/hr) | 410 | 410 | 410 | 440 | 440 | 380 | 380 | 410 | 370 | 400 | 370 |
| Sulfuric ester (Kg/hr) | | 240 | 300 | 210 | 300 | 340 | 130 | 190 | 220 | 330 | 390 | 230 |
| Caustic soda solution (Kg/hr) | | 59 | 89 | 36 | 71 | 100 | 23 | 54 | 41 | 71 | 71 | 24 |
| AI content (wt. %) | | 65 | 62 | 63 | 65 | 63 | 65 | 62.5 | 65 | 69.5 | 70 | 70 |
| Caustic soda content (v. AI wt. %) | | 0.05 | 0.06 | 0.04 | 0.03 | 0.05 | 0.04 | 0.08 | 0.07 | 0.1 | 0.02 | 0.04 |
| Viscosity (poise at 40° C.) | | 150 | 130 | 140 | 150 | 140 | 160 | 130 | 120 | 180 | 170 | 160 |
| Rate of sulfonation (v. raw material %) | | 96 | 92.5 | 93 | 96.5 | 92.5 | 96 | 93 | 96.5 | 95.5 | 96.5 | 98 |
| Color tone | | 35 | 80 | 70 | 34 | 60 | 34 | 75 | 35 | 70* | 50** | 20 |
| Evaluation | | o | x | x | o | x | o | x | o | o | o | o |

*The color tone of material sulfate is 70.
**The color tone of material sulfate is 50.

COMPARATIVE EXAMPLE

A sulfuric ester of a higher alcohol having $C_{12}$ as its principal ingredient (trade name: Conol 20P, average molecular weight: 187, manufactured by New Japan Chemical Co., Ltd.) and a caustic soda solution having a concentration of 26 wt.% were supplied to a mixer at the rates of 200 Kg/hr and 120 Kg/hr respectively. The effluent from the mixer was cooled to about 60° C. by means of a heat exchanger and then circulated to the mixer, during which a part thereof was taken out as a solution of sodium salt of sulfuric ester of higher alcohol.

The properties of the thus obtained solution of sodium salt of sulfuric ester of higher alcohol were evaluated: AI concentration 64 wt.%, free caustic soda 0.02 wt.% (Based on AI), viscosity 115 poise (40° C.), rate of sulfonation (Based on material alcohol) 92%, and color tone 75 [absorbancy $(\log I/I_0) \times 10^3$ at 10% concentration].

What is claimed is:

1. A process for manufacturing an aqueous solution or slurry containing from 60 to 75 wt. % of sulfate of higher alcohol or alkylene oxide adduct of said alcohol, which comprises, in step (a), neutralizing (A) sulfuric ester material selected from the group consisting of (1) sulfuric esters of higher alcohols having from 8 to 22 carbon atoms and (2) sulfuric esters of higher alcohols having from 8 to 22 carbon atoms and adducted with from 1 to 5 moles, on the average, per mole of said alcohol, of alkylene oxide having from 2 to 4 carbon atoms, by commingling said sulfuric ester material with (B) first aqueous caustic alkali solution in proportions effective to form a crude neutralization product containing from 45 to 55 wt. % of said sulfate and from 1.5 to 3.5 wt. % of unreacted caustic alkali, said crude neutralization product having a viscosity of less than 50 poise at 50° C.; then, in step (b), commingling said crude neutralization product with an additional quantity of said sulfuric ester material and with a highly concentrated second aqueous caustic alkali solution, wherein said additional quantity of said sulfuric ester material is from 30 to 100 parts by weight per 100 parts by weight of said crude neutralization product and the amount of said caustic alkali in said highly concentrated second caustic alkali solution is sufficient to neutralize said additional quantity of said sulfuric ester material, to form a solution or slurry containing from 60 to 75% by weight of said sulfate and less than 0.5% by weight of caustic alkali, based on the weight of said sulfate.

2. A process according to claim 1 wherein the viscosity of said solution or slurry is less than 200 poise.

3. A process according to claim 1 wherein said caustic alkali is caustic soda.

4. A process according to claim 3 wherein said alkylene oxide is ethylene oxide.

5. A process according to claim 1 wherein the concentration of the aqueous caustic alkali solution used in step (a) is in the range of from 10 wt.% to 25 wt.%.

6. A process according to claim 1 or claim 5 wherein the concentration of the highly concentrated caustic alkali solution used in step (b) is in the range of from about 30 wt.% to about 50 wt.%.

7. A process according to claim 1 wherein step (b) is performed at a temperature in the range of from 30° C. to 70° C.

* * * * *